(12) United States Patent
Khosravi et al.

(10) Patent No.: US 6,425,915 B1
(45) Date of Patent: *Jul. 30, 2002

(54) HELICAL MESH ENDOPROSTHESIS AND METHODS OF USE

(75) Inventors: Farhad Khosravi, San Mateo; Michael Hogendijk, Palo Alto; Michael R. Ross, Hillsborough, all of CA (US)

(73) Assignee: Endotex Interventional Systems, Inc., Cupertino, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/047,891

(22) Filed: Mar. 25, 1998

Related U.S. Application Data

(63) Continuation-in-part of application No. 08/820,212, filed on Mar. 18, 1997, now Pat. No. 5,824,053.

(51) Int. Cl.[7] .................................................. A61F 2/06
(52) U.S. Cl. ...................................... 623/1.22; 623/1.11
(58) Field of Search ................................ 623/1, 11, 12, 623/1.22, 1.36, 1.11, 1.15, 1.17, 1.2, 1.3, 1.31, 1.18

(56) References Cited

U.S. PATENT DOCUMENTS

| | | |
|---|---|---|
| 4,553,545 A | 11/1985 | Maass et al. |
| 4,655,771 A | 4/1987 | Wallsten et al. ............... 623/1 |
| 4,665,918 A | 5/1987 | Garza et al. |
| 4,739,762 A | 4/1988 | Palmaz |
| 4,886,062 A | 12/1989 | Wiktor |

(List continued on next page.)

FOREIGN PATENT DOCUMENTS

| | | |
|---|---|---|
| EP | 0 201 466 A2 | 3/1986 |
| EP | 0 554 082 A1 | 1/1993 |
| EP | 0 621 017 A1 | 4/1994 |

OTHER PUBLICATIONS

Richard A. Hillstead, USP 4,913,141—"Apparatus and Method for Placement of a Stent within a Subject Vessel", Issued Apr. 3, 1990, pp. 1–4, article from Intellectual Property Network web site—http://www.patents.ibm.com.

D. Maass et al., "Radiological Follow–up of Transluminally Inserted Vascular Endoprosthesis: An Experimental Study Using Expanding Spirals," *Radiology*, vol. 152, No. 3, pp. 659–663 (1984).

*Primary Examiner*—Glenn K. Dawson
(74) *Attorney, Agent, or Firm*—Lyon & Lyon LLP

(57) ABSTRACT

A stent including a helical mesh coil is provided having a substantially rectangular cross-section and a band width equal to at least one-quarter to one-third of the maximum expanded circumference of the stent. The helical mesh has a multiplicity of openings forming a lattice that preferably provides about 60% open space or more. Alternative embodiments of the stent include free ends that preferentially overlap neighboring turns of the coil, and integrally formed barbs that enhance resistance to localized compressive forces. Methods of deploying the helical mesh coil stent also provided.

21 Claims, 4 Drawing Sheets

U.S. PATENT DOCUMENTS

| | | | |
|---|---|---|---|
| 5,019,090 A | | 5/1991 | Pinchuk ................... 606/194 |
| 5,026,377 A | * | 6/1991 | Burton et al. ............... 606/108 |
| 5,147,370 A | | 9/1992 | McNamara et al. ........ 606/108 |
| 5,211,658 A | * | 5/1993 | Clouse ......................... 623/1 |
| 5,246,445 A | | 9/1993 | Yachia et al. ............... 606/108 |
| 5,314,444 A | | 5/1994 | Gianturco ................... 606/195 |
| 5,342,387 A | * | 8/1994 | Summers .................... 606/198 |
| 5,344,426 A | | 9/1994 | Lau et al. .................... 606/198 |
| 5,421,955 A | | 6/1995 | Lau et al. ...................... 216/48 |
| 5,423,885 A | | 6/1995 | Williams ....................... 623/1 |
| 5,441,515 A | | 8/1995 | Khosravi et al. ........... 606/194 |
| 5,443,500 A | | 8/1995 | Sigwart ......................... 623/1 |
| 5,476,505 A | | 12/1995 | Limon ........................... 623/1 |
| 5,484,444 A | * | 1/1996 | Braunschweiler et al. .. 606/108 |
| 5,540,713 A | | 7/1996 | Schnepp-Pesch et al. ... 606/198 |
| 5,551,954 A | | 9/1996 | Buscemi et al. ............... 623/1 |
| 5,556,413 A | | 9/1996 | Lam ............................ 606/198 |
| 5,607,478 A | | 3/1997 | Lentz et al. ................... 623/12 |
| 5,609,627 A | * | 3/1997 | Goicoechea et al. ........ 606/108 |
| 5,824,053 A | * | 10/1998 | Khosravi et al. .............. 623/1 |
| 5,830,229 A | | 11/1998 | Konya et al. |
| 6,063,111 A | * | 5/2000 | Hieshima et al. .......... 623/1.11 |
| 6,156,062 A | * | 12/2000 | McGuinness ............... 623/1.11 |
| 6,241,691 B1 | * | 6/2001 | Ferrera et al. ............... 600/585 |

\* cited by examiner

HELICAL MESH ENDOPROSTHESIS AND METHODS OF USE

The present application is a continuation-in-part of application Ser. No. 08/820,212, filed Mar. 18, 1997, now U.S. Pat. No. 5,824,053, issued Oct. 20, 1998, the disclosure of which is expressly incorporated herein by reference.

FIELD OF THE INVENTION

The present invention relates to vascular prostheses, commonly referred to as "stents," for maintaining the patency of a body vessel following a dilatation procedure, such as percutaneous transluminal coronary angioplasty. More specifically, the present invention relates to vascular prostheses formed of helical mesh coils, especially for use in exposed vessels and saphenous vein grafts.

BACKGROUND OF THE INVENTION

A number of vascular prostheses are known for use in maintaining the patency of a body lumen following a dilatation procedure. Generally, in a procedure such as percutaneous transluminal angioplasty, a balloon catheter is inserted transluminally to the site of a stenosis within an artery, and the balloon is dilated to crack the plaque lining the artery. To prevent the dilated artery from restenosing, it has become common practice to insert a vascular prosthesis, commonly referred to as a stent, within the artery to maintain the artery at the dilated diameter. For example, the Palmaz stent, sold by Cordis Inc., Miami Lakes, Florida, the Gianturco-Rubin stent sold by Cook Cardiology, Inc., Indianapolis, Ind., and the Multi-Link stent sold by Advanced Cardiovascular Systems, Inc., Santa Clara, Calif., are commonly used following angioplasty in such a manner.

The foregoing stents, which are generally described in U.S. Pat. No. 4,739,762 to Palmaz, the U.S. Pat. No. 5,314,444 to Gianturco, and U.S. Pat. 5,421,955 to Lau et al., respectively, are representative of many of the balloon expandable stent designs currently for being offered for sale or under development. These stent designs employ a rigid member that is deployed by plastically deforming the member using a dilatation element, such as a balloon catheter.

A drawback of plastically deformable stents, however, is that such prostheses cannot be used in vessels that are close to the surface of the patient, and therefore are unprotected against crushing blows (such vessels referred to hereinafter as "exposed vessels"). For example, if a plastically deformable stent is used in a carotid artery in the vicinity of the neck, even a minor neck injury could result in the stent collapsing in vivo, with potentially fatal consequences. Recent clinical trials of balloon expandable stents in exposed vessels have shown that up to 12% of the patients experience some collapse of the stent due to external forces.

Other stent designs which provide adequate. crush resistance are known, however, these previously known stent designs suffer from other drawbacks. For example, U.S. Pat. No. 5,443,500 to Sigwart and U.S. Pat. No. 5,344,426 to Lau et al. each describe a vascular prosthesis formed of a self-expanding coil sheet, while U.S. Pat. No. 5,423,885 to Williams describes a similar coiled sheet stent having a plurality of protrusions on its surface. A coiled sheet stent generally is rolled down to a small diameter, and then constrained within a delivery device at the small diameter. Once the stent is placed across a stenosis, a sheath of the delivery device is retracted, allowing the sheet to unroll. U.S. Pat. No. 5,556,413 to Lam describes a variation of a coiled sheet stent having a plurality of longitudinal slits so that the sheet forms helical coils when expanded. A drawback of coiled sheet prostheses, however, is that such prostheses generally are limited to use in vessels having relatively long lengths of uniform diameter, and which possess relatively low tortuosity.

U.S. Pat. No. 4,655,771 to Wallsten provides a woven wire tubular mesh member which is contracted to its delivery profile by elongating the stent. When the ends of the stent are released, the stent attains its expanded diameter by undergoing a considerable shortening of length. Drawbacks inherent in stents of this design include a limited range of diameters at which acceptable radial strength can be achieved, and relatively low longitudinal flexibility. In addition, the considerable shortening of the stent encountered during deployment can result in lack of precision during stent deployment.

U.S. Pat. No. 4,665,918 to Garza et al. describes a vascular prosthesis and delivery system for a self-expanding helical coil or coiled sheet. The helical coil is held in a constrained shape within an outer sheath of the delivery system, and is deployed by retracting the outer sheath. U.S. Pat. No. 5,147,370 to McNamara et al. describes a nitinol stent comprising a helical band having proximal and distal loops which is wound tightly onto a catheter and retained using a mandrel, so that the coil self-expands when released from restraint. U.S. Pat. No. 4,553,545 to Maass et al. describes similar helical coils formed from stainless steel and delivery systems therefore. All three of these patents suggest the use of a helical coil having a rectangular cross-section, while Maass further suggests that the coil may include punched openings to form a double helix structure.

While results of initial testing of helical band-type coil stents appeared promising, as described for example, in D. Maass et al., "Radiological Follow-up of Transluminally Inserted Vascular Endoprosthesis: An Experimental Study Using Expanding Spirals", Radiology 1984, Vol. 152, No. 3, pp. 659–663 (1984), concerns over the safety and efficacy of such designs have resulted in little effort to commercialize this technology. In particular, the tendency of the ends of the stent to project into the blood flow, as in the McNamara and Maass devices, is thought to promote thrombosis, while the large surface area contacted by the helical bands is thought to enhance restenosis.

Consequently, efforts to develop commercial systems using the coil-spring concept have concentrated on coiled springs made from nickel-titanium alloy wires, so as to minimize the contact area between the stent and the intima of the body vessel. For example, U.S. Pat. No. 5,246,445 to Yachia et al. (commercialized by Instent, Inc., Minneapolis, Minnesota), describes a helical wire coil that is drawn down onto a catheter for delivery by axially extending the catheter. The stent is deployed by releasing one end of the stent. U.S. Pat. No. 5,476,505 to Limon describes a similar helical wire coil stent.

Like the Wallsten device, the device described in the Yachia et al. patent experiences considerable longitudinal shortening during deployment. The device includes a further drawback that, as the device expands, the free end of the coil it believed to whip around the catheter at high speed. Because such behavior could dislodge pieces of plaque from the interior of the vessel wall, such stent designs appear unsuitable for use in the carotid arteries and in other vessels in which embolization presents a problem.

Previously known helical coil stent designs are thought to present a number of other drawbacks as well, such as having limited ranges of expanded diameters, the potential for tilting of coils and prolapse into gaps in a stenotic region, uneven expansion, migration, and thrombosis formation. For example, the devices described in the Maass et al. patent are expected to have only a limited range of expanded diameters due to the mechanical characteristics of stainless steel.

Likewise, the wire coils of the Yachia et al. device have been observed to expand unevenly, as well as to slip into cracks created in the plaque during the dilatation procedure, thereby creating nonuniform radial strength along the length of the stent and increasing the chance of restenosis. The smooth outer wall surface of the stents, as well as the narrowness of individual turns of the stent (both resulting from the use of coiled wire), also is thought to cause slipping and localized migration of turns, further reducing radial strength.

In addition, the potential for individual turns of the coil of the Yachia et al. device to project (either by tilting or overlapping neighboring turns) into the bloodstream, like the loops in the McNamara et al. device, enhances the risk for thrombosis. More generally, since the ends of a helical coil stent do not experience the same outward force as full turns of the coil, it is thought that the free ends may also project into the bloodstream, and hence serve as sites for thrombi formation.

In view of the foregoing, it would be desirable to provide a helical coil stent that overcomes the drawbacks of the previously known stents. In particular, it would be desirable to provide a helical coil stent that has uniform and reproducible radial strength over a range of expanded diameters.

It also would be desirable to provide a helical coil stent that conforms to a diameter of the body lumen, but which is crush resistant and will not experience localized slipping or migration of individual turns of the coil if loaded in compression after deployment.

It further would be desirable to provide a helical coil stent possessing a high degree of longitudinal flexibility so that it can be advanced through a tortuous body lumen, yet which has high radial strength over a range of expanded diameters and that experiences much less overall shortening during deployment then previously known helical coil stents.

It also would be desirable to provide a self-expanding helical coil stent that can be contracted to its delivery diameter with relatively few turns, so that the stent expands in a controlled manner without the high speed whipping action observed in previously known helical coil stents, thus reducing the risk of embolization.

SUMMARY OF THE INVENTION

In view of the foregoing, it is an object of the present invention to provide a helical coil stent that overcomes the drawbacks of the previously known stents relating to limited ranges of expanded diameters, tilting of coils and prolapse into gaps in a stenotic region, uneven expansion, migration, and thrombi formation.

It is therefore an object of the present invention to provide a helical coil stent that has uniform and reproducible radial strength over a range of expanded diameters.

It is another object of this invention to provide a helical coil stent that conforms to the diameter of the body lumen, but which is crush resistant and will not experience localized slipping or migration of individual turns of the coil if loaded in compression after deployment.

It is a further object of the invention to provide a helical coil stent possessing a high degree of longitudinal flexibility so that it can be advanced through a tortuous body lumen, yet which has high radial strength over a range of expanded diameters and that experiences much less overall shortening during deployment then previously known helical coil stents.

It is yet another object of this invention to provide a self-expanding helical coil stent that contracts to its delivery diameter with relatively few turns, so that the stent expands in a controlled manner without the high speed whipping action observed in previously known helical coil stents, thus reducing the risk of embolization.

These and other objects of the invention are accomplished by providing a stent comprising a self-expanding helical mesh coil having a substantially rectangular cross-section and a band width of at least about one-quarter of the maximum expanded circumference of the stent. The helical mesh has a multiplicity of openings forming a lattice which preferably provides about 60% open space or more. The openings serve to secure the stent within the body lumen, and serve to resist sliding or localized migration of the turns of the stent after deployment. In addition, the large band width of the helical mesh coil enables the stent to be reduced to its contracted diameter with very few turns, thereby providing controlled expansion without the whipping action associated with previously known stent designs.

Alternative embodiments of the helical mesh coil stent of the present invention may include specially designed free ends of the stent, which are treated to preferentially overlap neighboring turns of the coil when deployed, thereby ensuring that the free ends of the stent do not project into the body lumen. In addition, the helical mesh may include integrally formed barbs that, in addition to the multiplicity of openings, induce a ratcheting effect enabling the stent to resist localized compressive forces.

Methods and apparatus for deploying the helical mesh coil stent of the present invention are also provided. In accordance with these methods, the helical mesh coil stent is first deployed into a body lumen so that it expands when released to conform to the diameter of the body lumen. Delivery apparatus is provided that includes a retractable element for restraining either or both ends of the stent during deployment. The delivery apparatus also may serve to hold a first end of the stent in engagement with a wall of the body vessel during deployment, thereby enhancing accuracy of placement of the stent. A dilatation element (which may be tapered) is then disposed within the stent and expanded, thereby ensuring that the turns of the stent are uniformly expanded into contact with the intima of the body lumen. The large band width, in conjunction with the multiplicity of openings (and barbs, if present), serve to affix the stent in apposition to the body walls, without tilting or overlap.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention provides stents for treatment of intraluminal disease that overcome the limitations of previously known helical coil stents. In particular, an expanding helical mesh coil stent constructed in accordance with the present invention provides high radial strength uniformly over the length of the stent, while reducing the risk of tilted or overlapping coils found in previously known helical coil stent designs. In addition, the helical mesh coil stent of the present invention is highly flexible when in its contracted state, and highly crush resistant in its expanded state. The stent and methods of the present invention are believed to be especially useful in tapered vessels, such as regions of the coronary arteries, the carotid arteries, saphenous vein grafts and biliary ducts.

Figure 1:
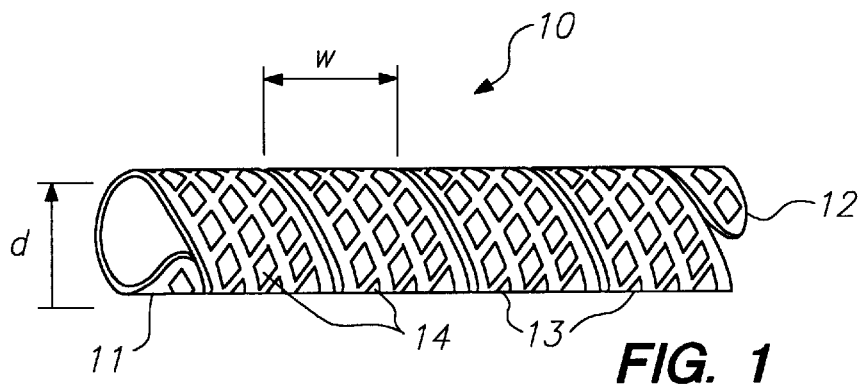
FIG. 1 is a perspective view of an illustrative helical mesh coil stent constructed in accordance present invention.

Referring to FIG. 1, stent 10 constructed in accordance the present invention is described. Stent 10 comprises a helical coil formed from a band or sheet having a substantially rectangular cross-section, as shown in FIGS. 2A–2D. The stent includes free ends 11 and 12 at the proximal and distal ends of the stent, respectively, and plurality of turns 13 including multiplicity of openings 14. When in its expanded state, preferably little or no gap exists between neighboring turns 13 of stent 10. Alternatively, the helical coil comprise a multiplicity of interwoven wires forming a band. The multiplicity of wires are welded together at the perimeter of the coil, and internal intersections of the wires also may be welded together.

A preferred embodiment of stent 10 may be satisfactorily employed in a number of body lumens over a range of expanded diameters, with width w of turns 13 preferably at least one-quarter of the maximum expanded diameter of the stent, or roughly about equal to the maximum expanded diameter d. Depending upon the pitch of turns 13, the turns may overlap one another when the stent is rolled down to its contracted state, thus reducing the overall length of the stent and improving trackability through tortuous vessels. As will be apparent to one of skill in the art, however, the lengths of the helical mesh coil, the pitch and the number of turns may be varied depending upon the intended application and desired mechanical characteristics of the stent.

Referring now to FIGS. 2A to 2D, stent 10 includes multiplicity of openings 14 arranged in a lattice that preferably comprises 60% or more of the surface of the stent. As shown in FIGS. 2A–2D, goopenings 14 may be regular polygons, such as triangular-shaped, diamond-shaped, rectangular-shaped or circular-shaped openings, or any combination thereof. In particular, the triangular-shaped lattice of openings 14 in FIG. 2A results in a metal contact area of about 40%, with 60% open space; the diamond-shaped lattice has a metal contact area of about 35% (65% open space); and the rectangular-shaped and circular-shaped lattices have metal contact areas of about 31% and 32% (69% and 68% open space), respectively.

Figure 2A:
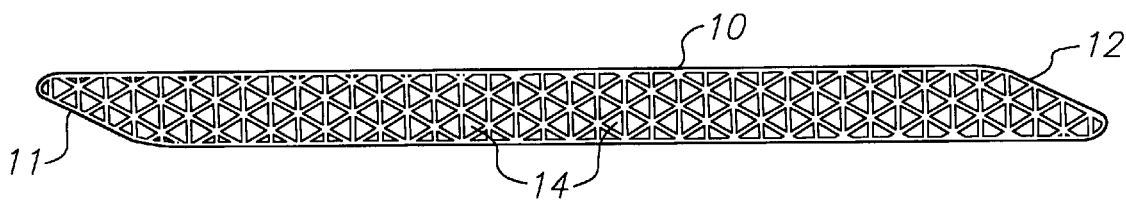
FIG. 2A is a plan view of a strip having a triangular-shaped lattice suitable for forming a helical mesh coil stent in accordance with the invention.
Figure 2B:
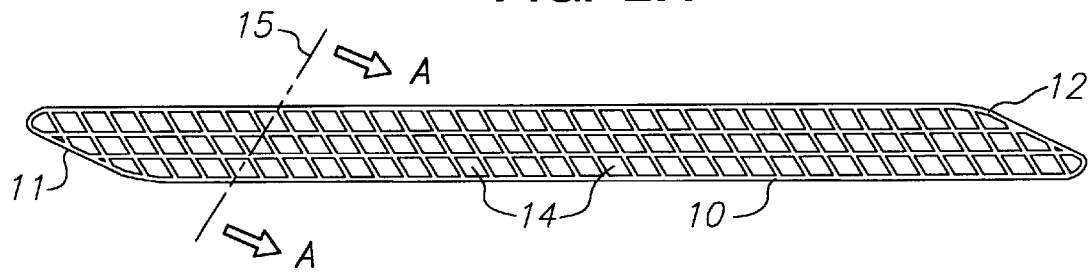
FIG. 2B is plan view of a strip having a diamond-shaped lattice suitable for forming a helical mesh coil stent in accordance with the invention.
Figure 2C:
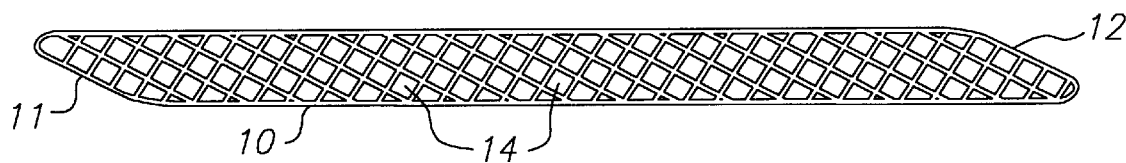
FIG. 2C is plan view of a strip having a rectangular lattice suitable for forming a helical mesh coil stent in accordance with the invention.
Figure 2D:
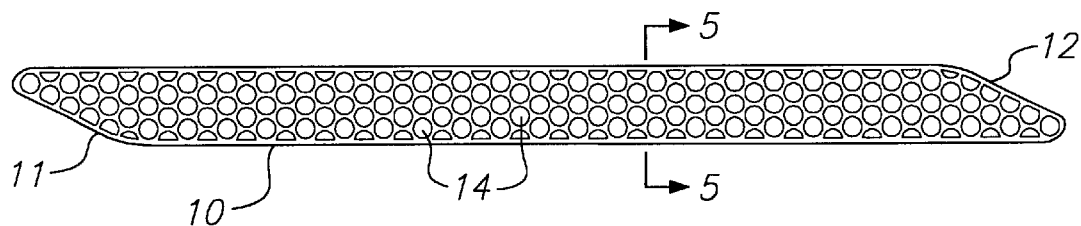
FIG. 2D is plan view of a strip having a circular lattice suitable for forming a helical mesh coil stent in accordance with the invention.

Openings 14 enable tissue lining the wall of the body lumen to grow through the openings to envelope the stent. In addition, openings 14 serve to fix the stent in position against localized slipping once the stent has been impressed into the intima of the body lumen using a mechanical expander, as described hereinafter. Based on testing of initial prototype stents 6 mm in diameter and 30 mm long (when deployed) the diamond-shaped lattice of FIG. 2B is thought to provide the highest radial strength.

Stent 10 generally comprises a thin (about 1–5 mils) band of a biocompatible material, such as a thermal shape-memory polymer or metal, super-elastic material such as a nickel-titanium alloy, or other biocompatible elastic material such as a stainless steel, tantalum, platinum or tungsten alloy. In a preferred embodiment, stent 10 comprises a nickel-titanium shape memory alloy having an austenite transition temperature slightly below body temperature.

Stent 10 is preferably formed from a flat sheet of nickel-titanium alloy, and multiplicity of openings 14 are formed therein by any of a number of conventional metal working processes, including die and punch, laser cutting, or chemical etching. In other embodiments, stent 10 may comprise a band formed by interweaving a multiplicity of wires, for example, as shown in U.S. Pat. No. 5,007,926 to Derbyshire. The multiplicity of wires are welded together at the perimeter of the band, and internal intersections of the wires also may be welded together. The band may be swaged to reduce its thickness.

For a stent made of a shape memory material, such as a nickel-titanium alloy, a band of suitable material is first formed into the shape depicted, for example, in FIG. 2B, by the methods described hereinabove. The sheet is then rolled about a mandrel (indicated by dotted line 15 in FIG. 2B) in a direction A (indicated by arrows in FIG. 2B) to form a coiled tubular member having an expanded shape as shown in FIG. 1. The coiled tubular member is then heat treated to activate the shape memory of the material. Stent 10 is then rolled to a contracted state for delivery by twisting free ends 11 and 12 in opposite directions.

When contracted, stent 10 may assume either an axially elongated shape, with adjacent turns of the stent lying adjacent to one another, or the adjacent coils may be configured to overlap one another. The latter configuration, wherein the coils overlap each other, is believed to be preferable to reduce overall change in the length of the stent during deployment.

Figure 3A:
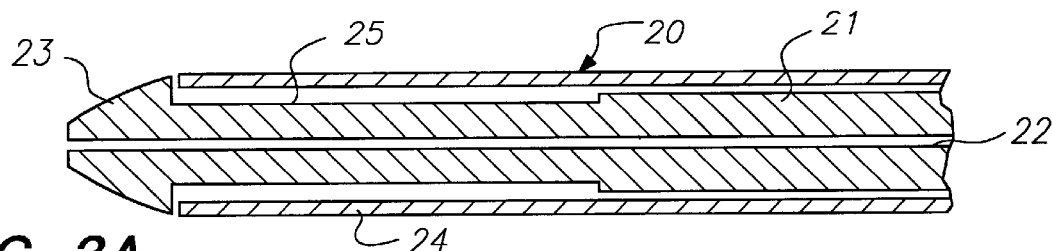
FIGS. 3A–3E are cross-sectional views of a delivery catheter having retractable and positioning elements suitable for use with the methods of the present invention.

Referring to FIGS. 3A–3D, various embodiments of delivery system 20 suitable for use with the stent and methods of the present invention are described. In FIG. 3A, delivery system 20 is similar to that disclosed in Garza et al. U.S. Pat. No. 4,665,918, and includes catheter 21 having central lumen 22 for accepting guide wire 200, nose cone 23 and outer sheath 24. Catheter 21 includes recess 25 that cooperates with outer sheath 24 to retain the stent in its contracted state for transluminal delivery. As is well-known in the art, delivery system 20 is inserted into a body lumen having a stenosis through a major vessel along a guide wire until the mid-point of the stent is located within the stenosis.

Figure 3B:
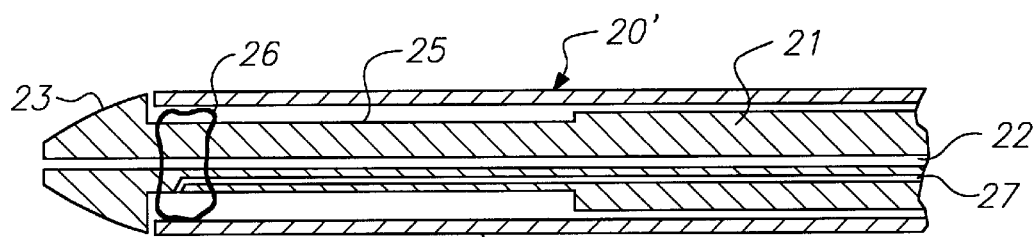

In FIG. 3B, delivery system 20' includes features 21–25 of delivery system 20 of FIG. 3A and further includes a positioning element consisting of compliant balloon 26 and inflation lumen 27. In accordance with the methods of the present invention, once the distal tip of outer sheath 24 has been partially retracted in a proximal direction to deploy the distal end of a stent, balloon 26 is inflated via inflation lumen 27. Inflation of balloon 26 urges the distal end of the stent into engagement with the wall of the body lumen. When the remaining portion of outer sheath 24 is then withdrawn, balloon 26 prevents axially displacement of the distal end of the stent, thereby ensuring accuracy in the placement of the stent.

Figure 3C:
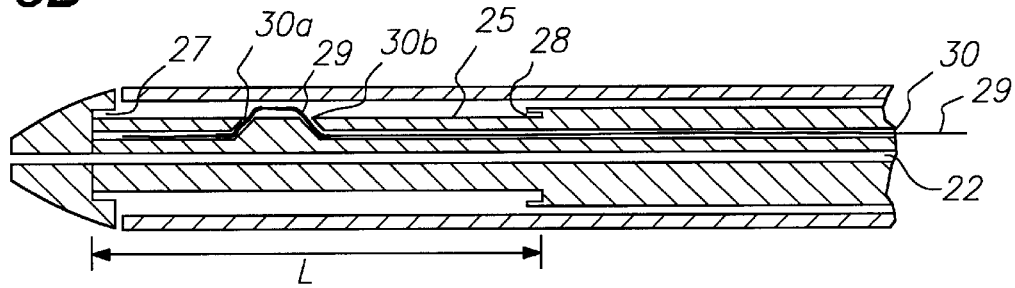

In FIG. 3C, delivery system 20" is similar to that of FIG. 3A but further includes recesses 27 and 28 at either end of recessed portion 25 of length L. Delivery system 20" further comprises retractable retaining element 29 disposed within lumen 30. Lumen 30 includes opening 30a where retaining element 29 exits lumen 30 and opening 30b where retaining element 29 re-enters lumen 30. Recesses 27 and 28 are configured to capture ends 11 and 12 of stent 10 (see FIG. 1), while retractable retaining element 29 loops over and captures an intermediate turn of the helical coil (not shown) against recessed portion 25 of catheter 21.

In accordance with the methods of the present invention, retractable element 29, which may be a flexible filament, thread or fine wire of stainless steel or nickel-titanium, serves to retain a stent in its contracted state for delivery. Once outer sheath 24 is retracted, retractable element 29 is withdrawn in the proximal direction, thereby permitting the central portion of the stent to expand. As the stent uncoils to a larger diameter, ends 11 and 12 are pulled free from recesses 27 and 28. Delivery catheter 20" therefore enhances the accuracy of the stent placement by enhancing the accuracy of placement of, for example, the mid-section of the stent, as opposed to an end of the stent as in FIG. 3B.

Figure 3D:
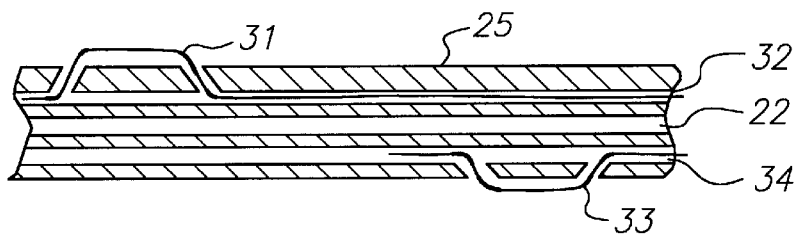
Figure 3E:
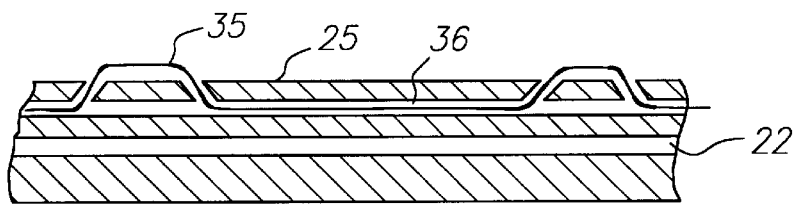

FIGS. 3D and 3E show alternative embodiments for securing the stent against length L of recessed portion 25 of catheter 21 for transluminal delivery, similar to the locking element disclosed in Sigwart U.S. Pat. No. 5,443,500. Unlike the locking element in the Sigwart patent, however, retaining elements of the present invention not only prevent the stent from unwinding, but also enable the clinician to control the direction of deployment of the stent.

In FIG. 3D, separate retaining elements 31 and 33 are employed to secure the distal and proximal ends, respectively, of stent 10 of FIG. 1. Retaining elements 31 and 33 are withdrawn proximally, preferably sequentially, so that the stent uncoils from catheter 21 in a preferred direction. In FIG. 3E, a single retaining element 35 is provided that captures both the distal and proximal ends of the stent. In FIG. 3E, the stent is deployed in a distal to proximal direction (after removal of outer sheath 24), while the separate retaining elements of the embodiment of FIG. 3D enable the stent to be deployed in either a distal-to-proximal or proximal-to-distal direction. As will of course be understood by one of skill in the art, compliant balloon 26 of the embodiment of FIG. 3B may be used in conjunction with any of the embodiments of FIGS. 3C–3E.

Figure 4A:
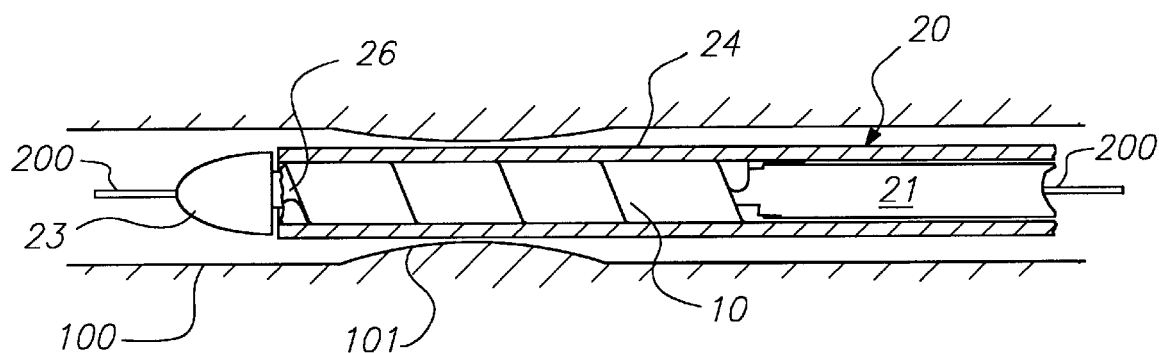
FIGS. 4A–4D are views showing the steps of deploying a stent constructed in accordance with the present invention.

Referring now to FIG. 4A, helical mesh coil stent 10 of FIG. 2B is shown rolled to its contracted state and disposed within delivery system 20' described hereinabove. Delivery system 20' generally is inserted into the body lumen after a dilatation device, such as a balloon catheter, has already been inserted and expanded within body lumen 100 to crack the deposits constituting stenosis 101. It is expected, however, that once the dilatation device is contracted, there may be some recoil of the stenosis, resulting in the bulge illustrated in FIG. 4A.

Figure 4B:
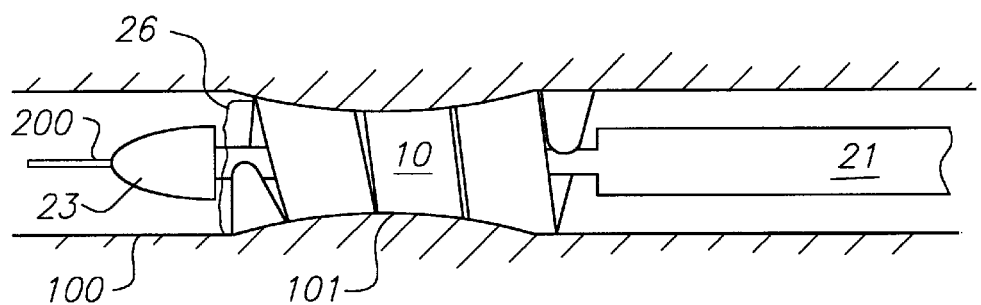

Once the location of delivery system 20' is established, for example, using fluoroscopy and standard angiographic techniques, sheath 24 of the delivery system is retracted to release a distal portion of helical mesh coil stent 10 into body lumen 100. Compliant balloon 26 is then inflated to anchor the distal turn of stent 10 against the inner surface of the body lumen, and sheath 24 is fully retracted. As seen in FIG. 4B, when released from sheath 24, the individual turns of stent 10 unwind to conform to the diameter of the body lumen. As noted above, while stenosis 101 has already been expanded, the segments of the plaque may still result in some unevenness of expansion of the stent (for clarity, this effect is exaggerated in FIG. 4B).

Because the stent of the present invention involves many fewer turns than previously known helical coil stents, it is contemplated that the expansion of the stent will not produce the whipping action observed in some previously known stent designs. The presence of fewer turns 13, together with the overlap of some of the turns when in the contracted state, is also expected to reduce the extent of shortening of the stent relative to previously known designs, thereby improving the accuracy of the stent placement. Moreover, the use of compliant balloon 26 is further expected to enhance accuracy of the stent placement, since it reduces axial displacement of the distal end of the stent during deployment.

Figure 4C:
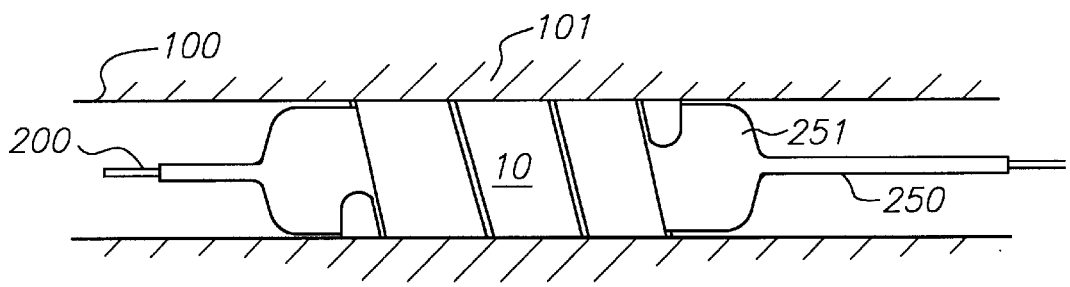

With respect to FIG. 4C, a mechanical expander, in the form of balloon catheter 250 carrying balloon 251, is transluminally inserted within stent 10. As balloon 251 expands, stent 10 further uncoils so that the stent conforms to the expanded shape of the balloon. Importantly, the step of conforming the helical mesh to the balloon shape involves a slight rotation of the ends 11 and 12 of the stent as the stent unwinds; however, this expansion does not involve plastic deformation of the helical mesh. In addition, as the balloon is expanded, it causes the open lattice of the stent to become embedded in the intima of the body lumen. When stent 10 is completely deployed, there preferably is little or no overlap, and little or no gap formation, between adjacent turns 13 of the helical mesh.

Figure 4D:
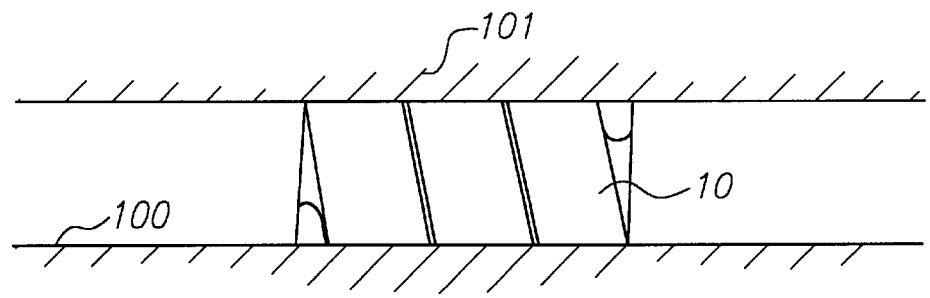

Once the stent has been embedded in the intima of the body lumen, balloon 251 is contracted, and balloon catheter 250 is withdrawn from the body lumen. Because the multiplicity of openings 14 tends to capture the vessel intima, stent 10 retains the shape impressed in it during the step of the balloon expansion, as illustrated in FIG. 4D, and does recoil elastically to the shape assumed when initially released from sheath 24.

Importantly, because stent 10 is elastically expanded and embedded in the intima of the body wall during dilation of the mechanical expander, the stent retains its elasticity and is capable of withstanding compressive loads without crushing, and without sliding or localized migration of turns 13, even when used in exposed vessels. Moreover, since the stent of the present invention preferably comprises a superelastic shape memory alloy, such as nickel-titanium, the stent may be conformed to a range of body lumen diameters and still provide acceptable radial strength.

Figure 5A:
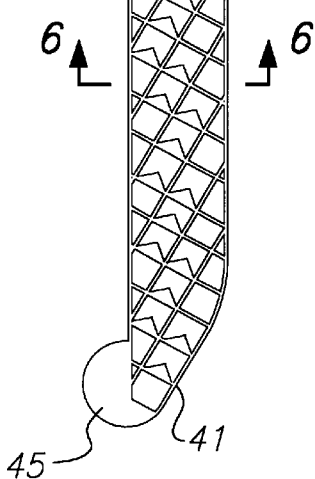
FIG. 5A is a plan view of a strip having plurality of barbs formed in the lattice and tabs that ensure the free ends of the stent are secured when deployed.
Figure 5B:
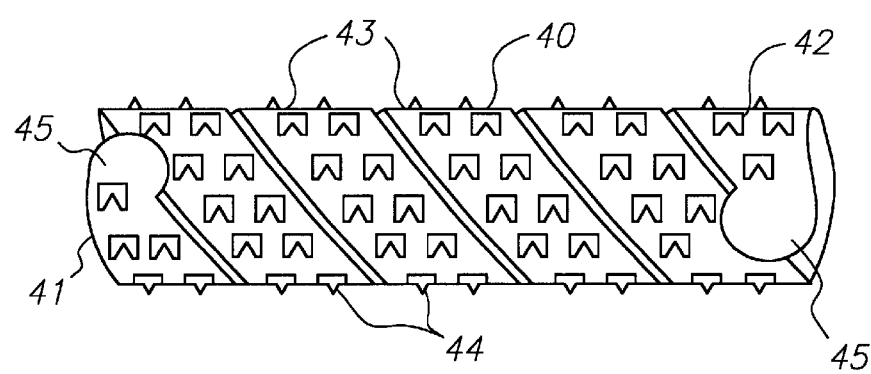
FIG. 5B is an elevation view of the strip of FIG. 5A when rolled into a helical mesh coil stent in accordance with the present invention.

Referring now to FIGS. 5A and 5B, an alternative embodiment of the stent of the present invention is described. Stent 40 comprises a helical mesh coil having a rectangular lattice (similar to the stent design of FIG. 2C), free ends 41 and 42, and plurality of turns 43. Stent 40 further comprises a multiplicity of barbs 44 integrally formed with the rectangular lattice, so that the barbs project outwardly from the stent when the band is rolled to form a tubular coil. Free ends 41 and 42 also include tabs 45 which overlap the neighboring turns of the stent, thereby fixing the free ends of the stent against the wall of the body lumen.

Stent 40 of FIGS. 5A and 5B is deployed in a manner similar to that described above with respect to FIGS. 4A to 4D. Barbs 44 are formed in the lattice of the helical sheet so that they engage the intima of the vessel wall only if the stent is loaded so as to wind the coil to a smaller diameter than its expanded diameter. In particular, the barbs are arranged so that when the balloon expands the stent from its initial deployment state in FIG. 4B by slightly unwinding the coil, the barbs do not engage the vessel wall. If however, a load is applied to stent 40 that would tend to reduce the stent wind to a smaller diameter, barbs 44 engage the vessel wall and resist compression of the stent. The barbs therefore provide a ratcheting effect, since they freely permit the stent to be expanded, but resist contraction.

Another feature of stent 40 is the presence of tabs 45 at each of free ends 41 and 42 of the stent. As illustrated in FIG. 5B, tabs 45 are treated, for example, by heat treatment during manufacture, to preferentially assume a position in which the tabs extend in an overlapping fashion outside the neighboring turns of the stent. In accordance with this feature of the invention, the free ends of stent 40 will be permanently affixed to the wall of the body lumen during the step of embedding the stent into the vessel wall with the mechanical expander. Accordingly, the free ends will be prevented from projecting into the body lumen, thus reducing the risk of thrombi formation. As will of course be understood by one of skill in the art, tabs 45 may be advantageously used on any of the helical mesh coil stents described hereinabove.

Figures 6A, 6B:
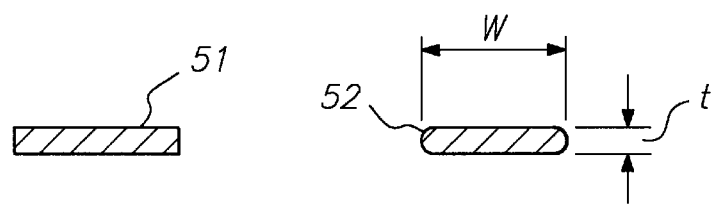
FIG. 6A and 6B are cross-sectional views of a turn of the helical mesh coil stent of the present invention.

Referring now to FIGS. 6A and 6B, a cross-section of stents 10 and 40 along the viewlines 6—6 is described (in which the internal detail has been omitted for clarity). In FIG. 6A, the band or sheet from which the stent is formed has a substantially rectangular cross-section with square edges 51, while in FIG. 6B, edges 52 of the sheet are rounded. The use of a band having rounded edges 52 may be beneficial, for example, to reduce the risk of injuring tissue pinched between gaps that may form between the turns of the coil, especially prior to the step of expanding the stent with the mechanical expander. Because the widths w of the bands in both FIGS. 6A and 6B are much greater than the thicknesses t, both designs constitute substantially rectangular cross-sections within the meaning of the present invention.

It is contemplated that a stent constructed in accordance with the present invention, for example, as shown in FIGS. 2A–2D, unlike conventional coiled sheet stents, may be disposed in a tapered lumen. In such applications, the mechanical expander may include a slight taper so that when the balloon is expanded, the stent adopts the taper of the balloon when it is embedded in the vessel wall. In addition, or alternatively, the stent of the present invention may also be formed as a tapered band or strip, i.e., a strip having a variable width along its length. In this case, the stent may be formed into a frustoconical tubular member using a tapered mandrel. After its initial expansion, the resulting stent may then be fully deployed using a tapered mechanical expander.

While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. A stent for supporting a body lumen, the stent comprising:
    a helical mesh coil comprising a plurality of turns and first and second free ends, the stent having a maximum expanded diameter, each turn having a substantially rectangular cross-section,
    the helical mesh coil being biased to an expanded state wherein neighboring turns between the first and second free ends have no overlap, the helical mesh coil having a pitch sufficient to prevent formation of gaps between neighboring turns in the expanded state, the helical mesh coil being reducible to a contracted state wherein at least some of the neighboring turns telescope within one another to facilitate delivery within a body lumen.

2. The stent as defined in claim 1, wherein each turn of the helical mesh coil has a width of at least about one-quarter of the maximum expanded circumference of the stent.

3. The stent as defined in claim 1, wherein the helical mesh coil comprises a lattice formed of a multiplicity of openings.

4. The stent as defined in claim 1, wherein the helical mesh coil comprises edges between the neighboring turns that are free from projections.

5. The stent as defined in claim 4, wherein the edges are squared or rounded.

6. A stent for supporting a body lumen, the stent comprising:
    a helical mesh coil comprising a plurality of turns and first and second free ends, the stent having a maximum expanded diameter, each turn having a substantially rectangular cross-section,
    the helical mesh coil comprising an expanded state wherein neighboring turns between the first and second free ends have no overlap and little or no gaps therebetween, the helical mesh coil being reducible to a contracted state to facilitate delivery within a body lumen,
    wherein the first and second free ends include tabs that overlap neighboring turns of the helical mesh coil for fixing the free ends of the helical mesh coil.

7. A method for supporting a body lumen, the method comprising the steps of:
    providing a stent comprising a helical mesh coil having first and second free ends, a maximum expanded circumference, and a plurality of turns, the stent being rolled to a contracted state of reduced diameter wherein at least some of the neighboring tunis telescope within one another;
    retaining the stent in the contracted state while transluminally inserting the stent to a desired location in a body lumen; and
    expanding the stent from the contracted state to an expanded state conforming to the shape of the body lumen at the desired location, the helical mesh coil having no overlap and having a pitch sufficient to prevent formation of gaps between neighboring turns in the expanded state.

8. The method as defined in claim 7, further comprising dilating the body lumen with a dilatation device prior to expanding the stent.

9. The method as defined in claim 7, wherein the step of expanding the stent comprises the steps of:
    expanding the stent using a mechanical expander so that the stent conforms to the shape of the mechanical expander and engages an interior wall of the body lumen; and removing the mechanical expander.

10. The method as defined in claim 7, wherein the step of expanding the stent comprises:
   releasing a portion of the stent from the contracted state;
   securing the released portion of the stent against an interior wall of the body lumen; and
   releasing the rest of the stent from the contracted state, the stent expanding to the expanded state, the secured portion of the stent experiencing no substantial axial displacement.

11. A method for supporting a body lumen, the method comprising steps of:
   providing a stent comprising a helical mesh coil having first and second free ends, a maximum expanded circumference, and a plurality of turns, the stent being rolled to a contracted state of reduced diameter;
   retaining the stent in the contracted state while transluminally inserting the stent to a desired location in a body lumen;
   releasing a portion of the stent from the contracted state;
   applying an engagement force to the released portion of the stent to secure it against an interior wall of the body lumen; and
   releasing the rest of the stent from the contracted state, the stent expanding to an expanded state conforming to the shape of the body lumen at the desired location, the secured portion of the stent experiencing no substantial axial displacement.

12. A method for supporting a body lumen, the method comprising steps of:
   providing a stent comprising a helical mesh coil having first and second free ends, a maximum expanded circumference, and a plurality of turns, the stent being rolled to a contracted state of reduced diameter;
   retaining the stent in the contracted state while transluminally inserting the stent to a desired location in a body lumen;
   releasing a portion of the stent from the contracted state;
   securing the released portion of the stent against an interior wall of the body lumen; and
   releasing the rest of the stent from the contracted state, the stent expanding to an expanded state conforming to the shape of the body lumen at the desired location, the secured portion of the stent experiencing no substantial axial displacement,
   wherein the step of releasing the rest of the stent comprises the steps of:
      expanding the stent using a mechanical expander so that the stent engages an interior wall of the body lumen; and
      removing the mechanical expander.

13. A method for supporting a body lumen, the method comprising steps of:
   providing a stent comprising a helical mesh coil having first and second free ends, a maximum expanded circumference, and a plurality of turns, the stent being rolled to a contracted state of reduced diameter;
   retaining the stent in the contracted state while transluminally inserting the stent to a desired location in a body lumen;
   releasing a portion of the stent from the contracted state;
   securing the released portion of the stent against an interior wall of the body lumen; and
   releasing the rest of the stent from the contracted state, the stent expanding to an expanded state conforming to the shape of the body lumen at the desired location, the secured portion of the stent experiencing no substantial axial displacement,
   wherein the retaining step comprises retaining the first and second free ends of the stent with a thread-like retractable and flexible retaining element.

14. The method of claim 13, wherein at least one of the releasing steps comprises withdrawing proximally at least part of the retaining element.

15. A method for supporting a body lumen, the method comprising steps of:
   providing a stent comprising a helical mesh coil having first and second free ends, a maximum expanded circumference, and a plurality of turns, the stent being rolled to a contracted state of reduced diameter;
   retaining the stent in the contracted state while transluminally inserting the stent to a desired location in a body lumen;
   releasing a portion of the stent from the contracted state;
   securing the released portion of the stent against an interior wall of the body lumen; and
   releasing the rest of the stent from the contracted state, the stent expanding to an expanded state conforming to the shape of the body lumen at the desired location, the secured portion of the stent experiencing no substantial axial displacement,
   wherein the retaining step comprises retaining the first and second free ends of the stent with first and second thread-like retractable and flexible retaining elements.

16. The method of claim 15, wherein the first releasing step comprises withdrawing the first retaining element, and the second releasing step comprises withdrawing the second retaining element.

17. A method for supporting a body lumen, the method comprising steps of:
   providing a stent comprising a helical mesh coil having first and second free ends, a maximum expanded circumference, and a plurality of turns, the stent being rolled to a contracted state of reduced diameter;
   retaining the stent in the contracted state while transluminally inserting the stent to a desired location in a body lumen;
   releasing a portion of the stent from the contracted state;
   securing the released portion of the stent against an interior wall of the body lumen; and
   releasing the rest of the stent from the contracted state, the stent expanding to an expanded state conforming to the shape of the body lumen at the desired location, the secured portion of the stent experiencing no substantial axial displacement,
   wherein the retaining step comprises:
      retaining the first and second free ends of the stent with first and second recess elements; and
      retaining a mid-section portion of the stent between the first and second free ends of the stent with a thread-like retractable and flexible retaining element.

18. The method of claim 17, wherein the first releasing step comprises withdrawing the retaining element.

19. A stent for supporting a body lumen, the stent comprising:
   a helical coil comprising a plurality of turns and first and second free ends, the helical coil being expandable from a contracted state to an expanded state, each turn having a substantially rectangular cross-section,
   wherein a plurality of adjacent turns of the helical coil telescope within one another in the contracted state, the plurality of adjacent turns do not overlap one another in the expanded state, and the plurality of turns comprise a width of at least about one quarter of a maximum expanded circumference in the expanded state. adjacent turns.

20. A stent for supporting a body lumen, the stent comprising:
 a helical coil comprising a plurality of turns and first and second free ends, the helical coil being expandable from a contracted state to an expanded state, each turn having a substantially rectangular cross-section,
 wherein a plurality of adjacent turns of the helical coil telescope within one another in the contracted state, the plurality of adjacent turns do not overlap one another in the expanded state, and at least one of the first and second ends has a width less than a width of the plurality of turns between the first and second ends.

21. A stent for supporting a body lumen, the stent comprising:
 a helical coil comprising a plurality of turns and first and second free ends, the helical coil being expandable from a contracted state to an expanded state,
 wherein a plurality of adjacent turns of the helical coil telescope within one another in the contracted state, the plurality of adjacent turns do not overlap one another in the expanded state, and at least one of the first and second ends are tapered.

* * * * *